(12) United States Patent
Field et al.

(10) Patent No.: US 9,658,143 B1
(45) Date of Patent: May 23, 2017

(54) OFFLINE MIXING

(71) Applicants: Paul Field, Papillion, NE (US); Kyle W. Uhlmeyer, Omaha, NE (US)

(72) Inventors: Paul Field, Papillion, NE (US); Kyle W. Uhlmeyer, Omaha, NE (US)

(73) Assignee: Elemental Scientific, Inc., Omaha, NE (US)

( * ) Notice: Subject to any disclaimer, the term of this patent is extended or adjusted under 35 U.S.C. 154(b) by 450 days.

(21) Appl. No.: 14/212,574

(22) Filed: Mar. 14, 2014

Related U.S. Application Data

(60) Provisional application No. 61/790,609, filed on Mar. 15, 2013.

(51) Int. Cl.
*G01N 1/38* (2006.01)
(52) U.S. Cl.
CPC ..................................... *G01N 1/38* (2013.01)
(58) Field of Classification Search
None
See application file for complete search history.

(56) References Cited

U.S. PATENT DOCUMENTS

| | | | | |
|---|---|---|---|---|
| 3,869,068 | A | * | 3/1975 | Chen .......................... G01N 1/38 141/25 |
| 4,610,170 | A | * | 9/1986 | Ekholm .................... G01N 1/38 436/179 |
| 4,946,795 | A | * | 8/1990 | Gibbons ............. B01F 13/0059 422/514 |
| 7,998,434 | B2 | * | 8/2011 | Shaw ........................ G01N 1/38 250/288 |
| 2002/0006668 | A1 | * | 1/2002 | Takahashi ................ G01N 1/38 436/180 |
| 2006/0133964 | A1 | * | 6/2006 | Bailey ....................... G01N 1/34 422/400 |
| 2012/0103075 | A1 | * | 5/2012 | Cormier ................... F04B 13/02 73/61.55 |

FOREIGN PATENT DOCUMENTS

JP              402122269         *   5/1990

* cited by examiner

*Primary Examiner* — Robert R Raevis
(74) *Attorney, Agent, or Firm* — Advent, LLP

(57) ABSTRACT

A method for diluting a sample includes drawing an aliquot of the sample past a mixing junction. The method also includes supplying the sample to the mixing junction and supplying a second fluid to the mixing junction. The second fluid mixes with the sample at the mixing junction to generate a diluted sample. The method further includes supplying the diluted sample from the mixing junction.

18 Claims, 5 Drawing Sheets

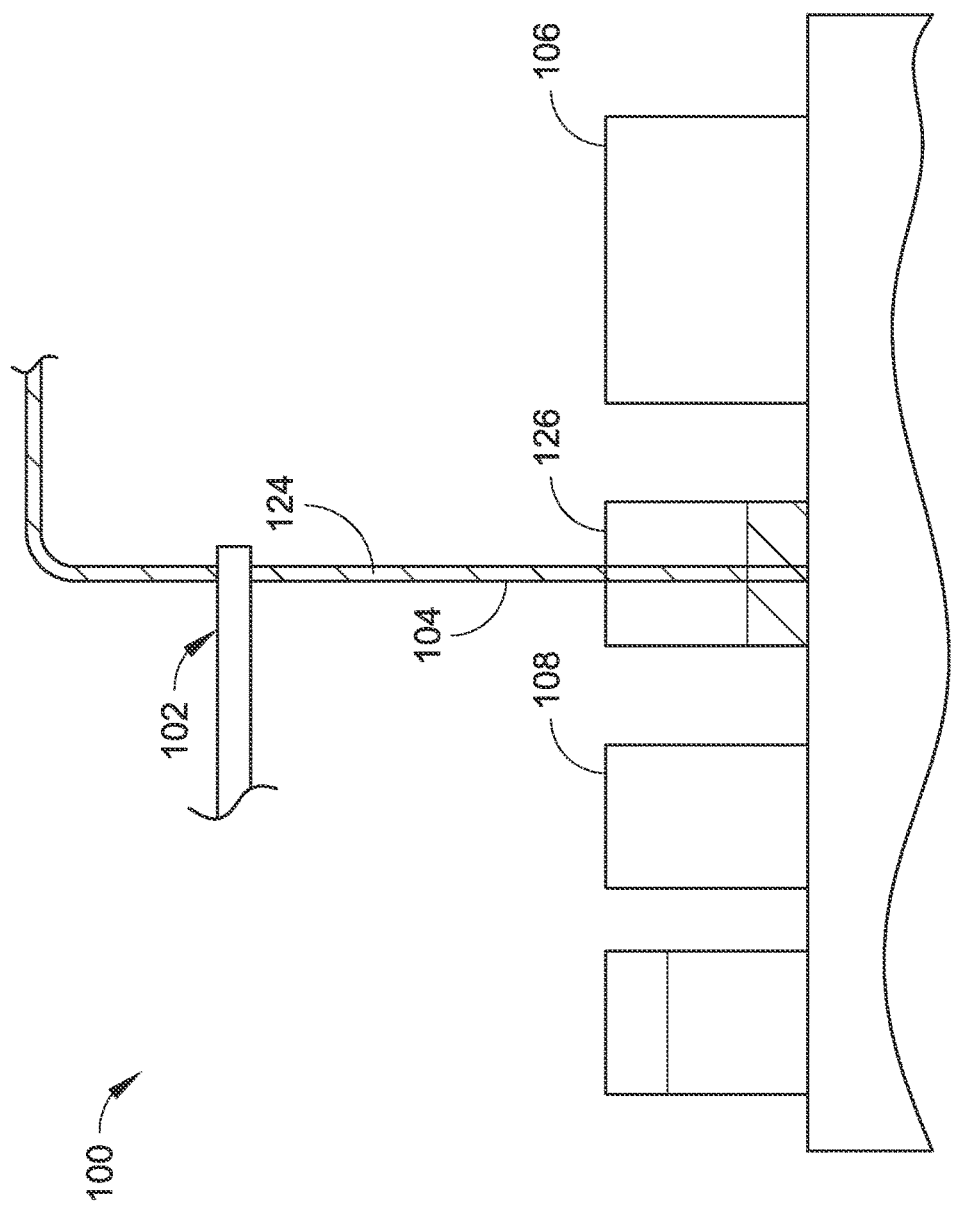

OFFLINE MIXING

SUMMARY

A method for diluting a sample includes drawing an aliquot of the sample past a mixing junction. The method also includes supplying the sample to the mixing junction and supplying a second fluid to the mixing junction. The second fluid mixes with the sample at the mixing junction to generate a diluted sample. The method further includes supplying the diluted sample from the mixing junction.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

DRAWINGS

The Detailed Description is described with reference to the accompanying figures. The use of the same reference numbers in different instances in the description and the figures may indicate similar or identical items.

FIG. 5 is a diagrammatic illustration of an autosampler assembly, where the autosampler assembly is configured to provide a diluted sample to a sample vial in accordance with example embodiments of the present disclosure.

DETAILED DESCRIPTION

Figure 1:
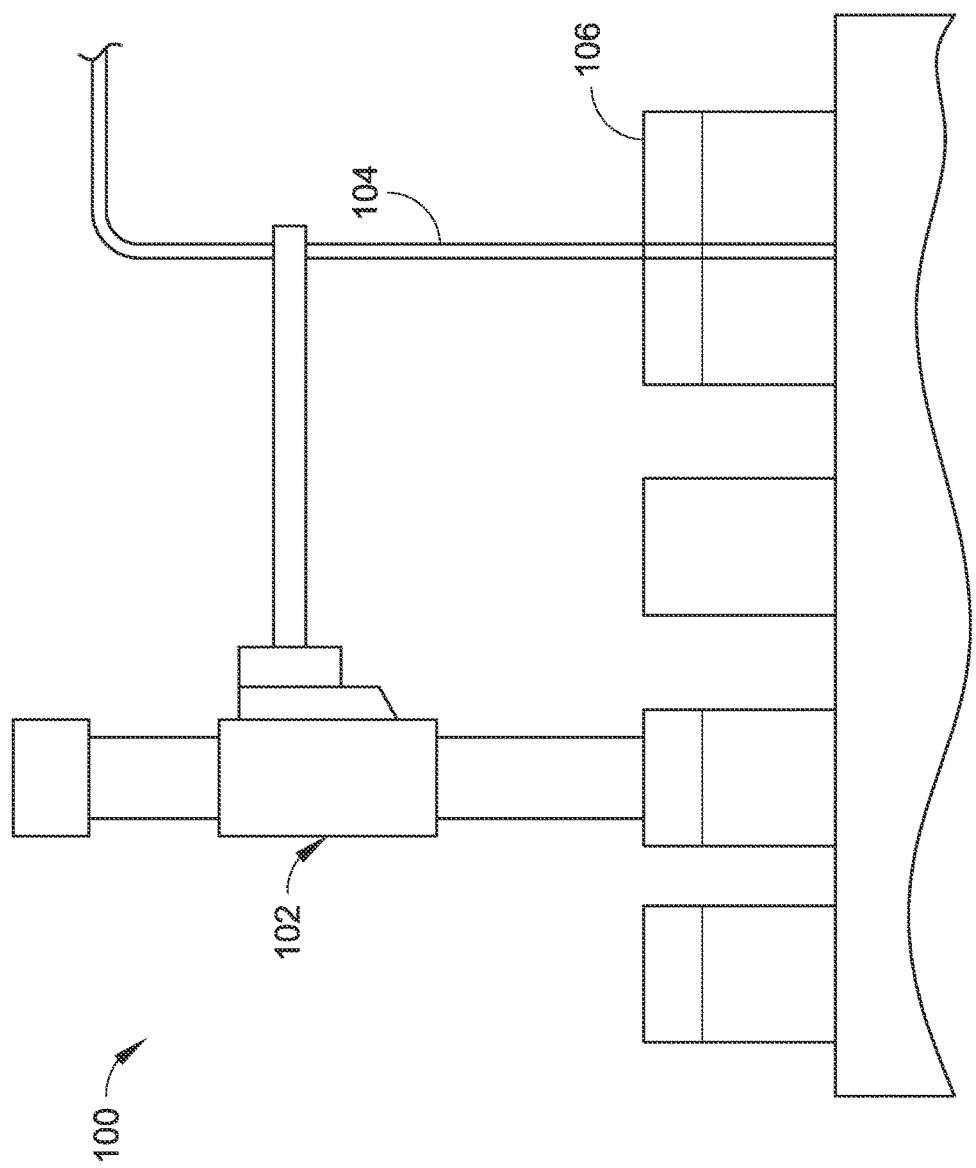
FIG. 1 is a diagrammatic illustration of an autosampler assembly, where the autosampler assembly is configured to rinse a sample probe at a rinsing station in accordance with example embodiments of the present disclosure.
Figure 2:
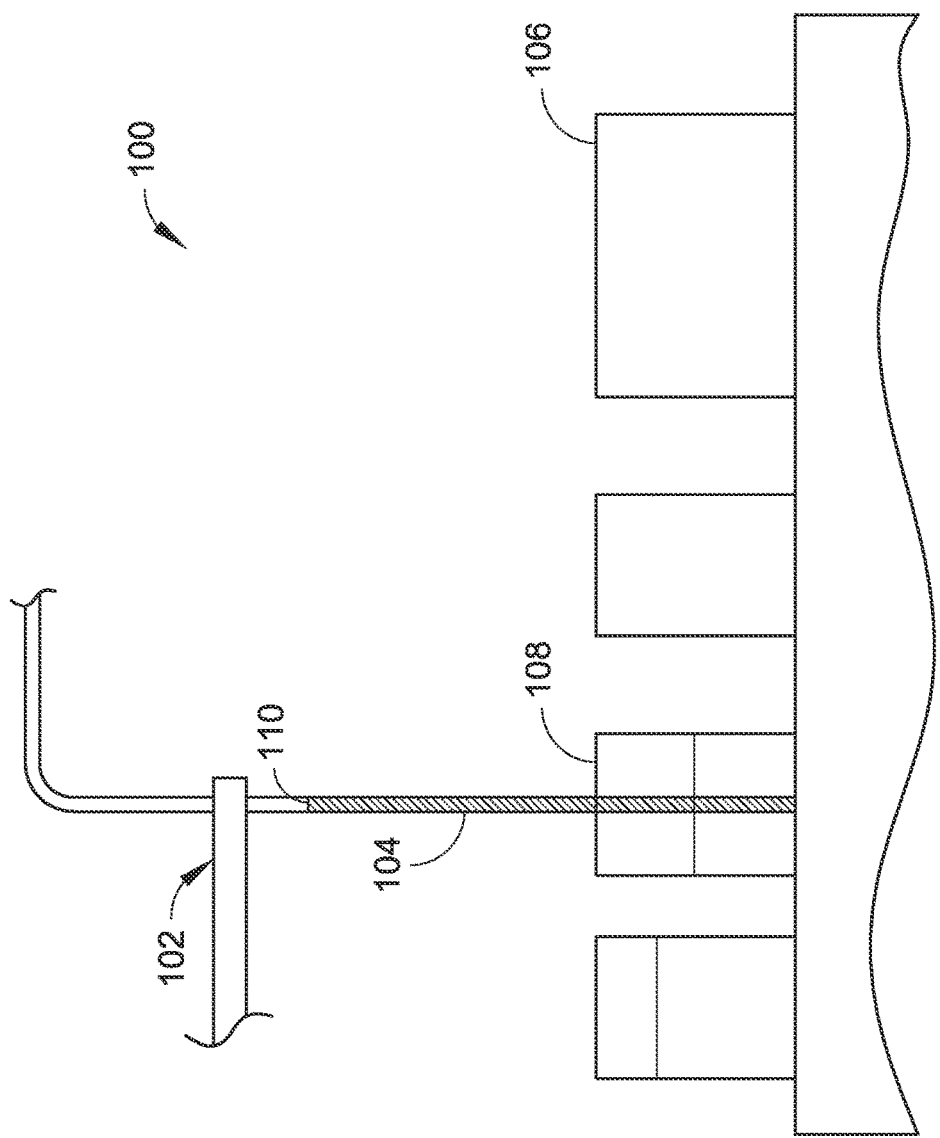
FIG. 2 is a diagrammatic illustration of an autosampler assembly, where the autosampler assembly is configured to insert a sample probe to collect a sample from a sample vial in accordance with example embodiments of the present disclosure.
Figure 3:
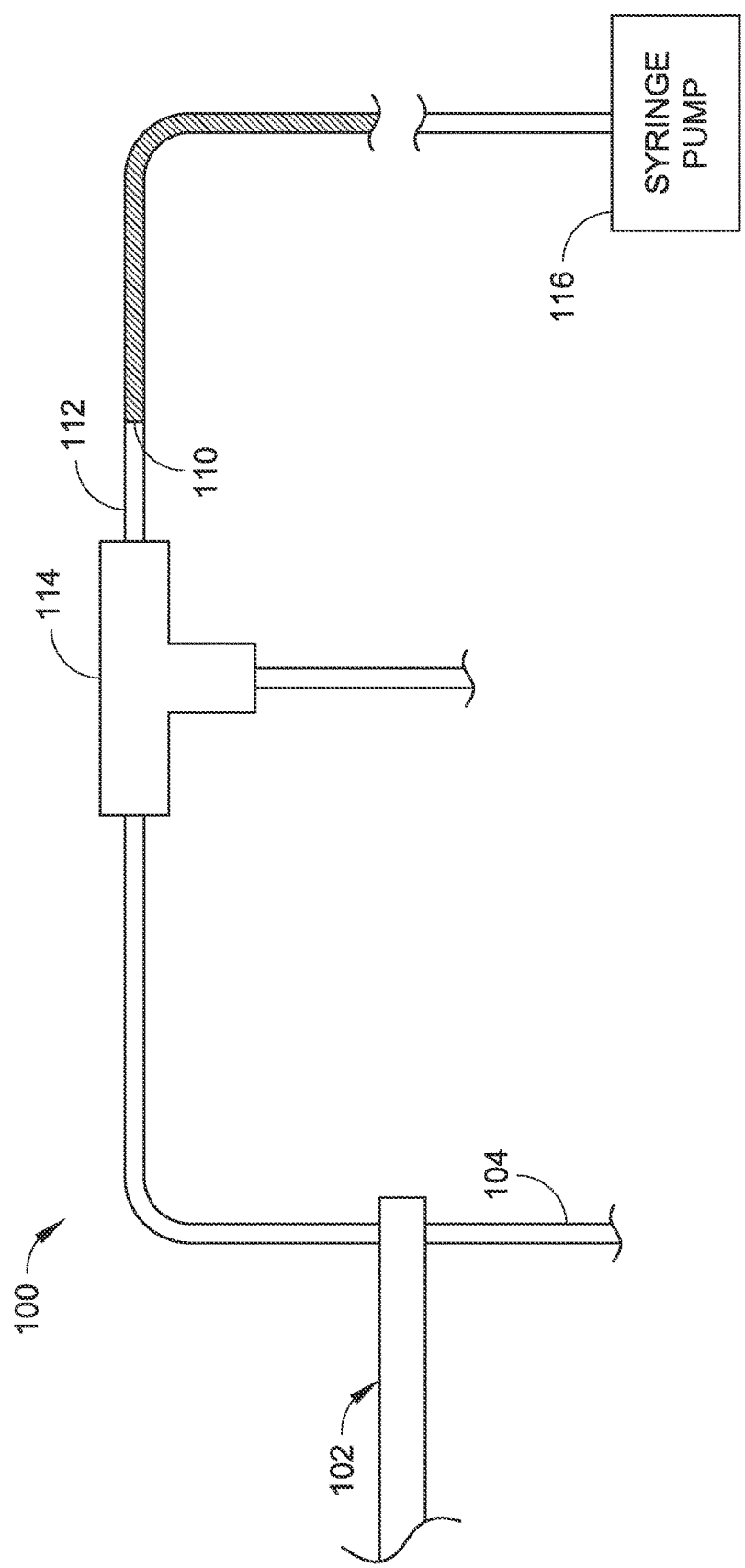
FIG. 3 is a diagrammatic illustration of an autosampler assembly, where the autosampler assembly is configured to draw a sample from a sample vial past a mixing junction in accordance with example embodiments of the present disclosure.
Figure 4:
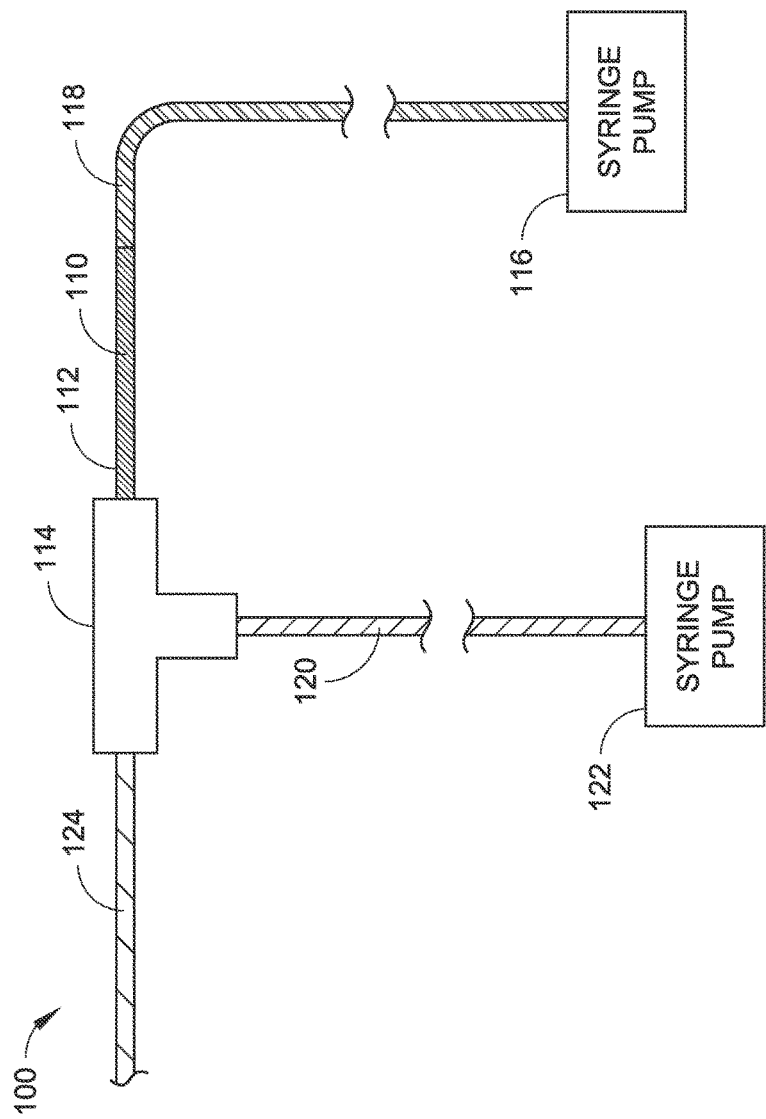
FIG. 4 is a diagrammatic illustration of an autosampler assembly, where the autosampler assembly is configured mix a sample with another fluid at a mixing junction in accordance with example embodiments of the present disclosure.

Referring to FIGS. 1 through 5, a system 100 for performing offline mixing is described. The system 100 includes a sampling assembly (e.g., autosampler assembly 102) having a sample probe 104 for collecting samples (e.g., from a sample vial of the autosampler assembly 102). As shown in FIG. 1, the sample probe 104 is rinsed at rinsing station 106. As shown in FIG. 2, the sample probe 104 is inserted into a sample vial 108 to collect a sample 110 from the sample vial 108. As shown in FIG. 3, a volume of the sample 110 (e.g., an aliquot) is drawn into a sample line 112 of the system 100 past a mixing junction (e.g., a tee 114). In embodiments of the disclosure, the aliquot of the sample 110 is drawn into the sample line 112 past the tee 114 by a pump (e.g., a syringe pump 116). As shown in FIG. 4, the sample 110 is then pushed back through the sample line 112 to the tee 114 (e.g., by a carrier fluid 118 pumped by the syringe pump 116). At the tee 114, the sample 110 is mixed with another fluid (e.g., a diluent 120). In embodiments of the disclosure, the diluent 120 is pushed to the tee 114 by a pump (e.g., a syringe pump 122). The diluent 120 is supplied at a flow rate to provide a predetermined amount of the diluent 120 with respect to the volume of the sample 110. In this manner, a predetermined dilution of the sample 110 is provided, and the diluted sample 124 is supplied from the tee 114. As shown in FIG. 5, the diluted sample 124 is then supplied to a sample vial 126 of the autosampler assembly 102 where it is collected. In this manner, offline mixing of the sample 110 is provided by the system 100.

Although the subject matter has been described in language specific to structural features and/or process operations, it is to be understood that the subject matter defined in the appended claims is not necessarily limited to the specific features or acts described above. Rather, the specific features and acts described above are disclosed as example forms of implementing the claims.

What is claimed is:

1. A method for diluting a fluid sample comprising:
    drawing an aliquot of the fluid sample from a first fluid line past a mixing junction and into a second fluid line using a first syringe pump;
    supplying the aliquot back to the mixing junction through the second fluid line using the first syringe pump;
    supplying a second fluid, via a second syringe pump, through a third fluid line to the mixing junction to mix the aliquot and the second fluid at the mixing junction and generate a diluted sample, the mixing junction coupled to each of an end of the first fluid line, an end of the second fluid line, and an end of the third fluid line, the end of the third fluid line and the end of the second fluid line having a cross-flow orientation with respect to each other; and
    supplying the diluted sample from the mixing junction.

2. The method as recited in claim 1, wherein the second fluid is supplied to the mixing junction at a predetermined flow rate to furnish a predetermined dilution to the diluted sample.

3. The method as recited in claim 1, wherein the mixing junction comprises a tee.

4. The method as recited in claim 1, wherein supplying the aliquot back to the mixing junction through the second fluid line using the first syringe pump comprises supplying the aliquot back to the mixing junction using a carrier fluid.

5. The method as recited in claim 1, wherein drawing an aliquot of the fluid sample from a first fluid line past the mixing junction comprises drawing the aliquot of the fluid sample past the mixing junction using a sampling assembly having a sample probe.

6. The method as recited in claim 5, wherein the sampling assembly comprises an autosampler assembly.

7. A system for diluting a fluid sample comprising:
    a mixing junction;
    a first pump coupled with the mixing junction, the first pump operable to draw an aliquot of the fluid sample from a first fluid line past the mixing junction and into a second fluid line and then supply the aliquot back to the mixing junction via the second fluid line; and
    a second pump coupled with the mixing junction, the second pump operable to supply a second fluid through a third fluid line to the mixing junction to mix the aliquot and the second fluid at the mixing junction and generate a diluted sample, the mixing junction coupled to each of an end of the first fluid line, an end of the second fluid line, and an end of the third fluid line, the end of the third fluid line and the end of the second fluid line having a cross-flow orientation with respect to each other, the first pump and second pump operable to supply the diluted sample from the mixing junction.

8. The system as recited in claim 7, wherein the second pump is operable to supply the second fluid to the mixing junction at a predetermined flow rate to furnish a predetermined dilution to the diluted sample.

9. The system as recited in claim 7, wherein the mixing junction comprises a tee.

10. The system as recited in claim 7, wherein at least one of the first pump or the second pump comprises a syringe pump.

11. The system as recited in claim 7, wherein the first pump is coupled with a carrier fluid and supplies the aliquot back to the mixing junction via the second fluid line using the carrier fluid.

12. The system as recited in claim 7, further comprising a sampling assembly having a sample probe, the sample probe in fluid communication with the first pump for drawing the aliquot of the fluid sample past the mixing junction.

13. The system as recited in claim 7, wherein the sampling assembly comprises an autosampler assembly.

14. A system for diluting a fluid sample comprising:
a mixing junction;
a first syringe pump coupled with the mixing junction, the first syringe pump operable to draw an aliquot of the fluid sample from a first fluid line past the mixing junction and into a second fluid line and then supply the aliquot back to the mixing junction via the second fluid line;
a sampling assembly having a sample probe, the sample probe in fluid communication with the first syringe pump for drawing the aliquot of the fluid sample from the first fluid line past the mixing junction; and
a second syringe pump coupled with the mixing junction, the second syringe pump operable to supply a second fluid through a third fluid line to the mixing junction to mix the aliquot and the second fluid at the mixing junction and generate a diluted sample, the mixing junction coupled to each of an end of the first fluid line, an end of the second fluid line, and an end of the third fluid line, the end of the third fluid line and the end of the second fluid line having a cross-flow orientation with respect to each other, the first syringe pump and second syringe pump operable to supply the diluted sample from the mixing junction.

15. The system as recited in claim 14, wherein the second syringe pump is operable to supply the second fluid to the mixing junction at a predetermined flow rate to furnish a predetermined dilution to the diluted sample.

16. The system as recited in claim 14, wherein the mixing junction comprises a tee.

17. The system as recited in claim 14, wherein the first syringe pump is coupled with a carrier fluid and supplies the aliquot back to the mixing junction via the second fluid line using the carrier fluid.

18. The system as recited in claim 14, wherein the sampling assembly comprises an autosampler assembly.

* * * * *